United States Patent
Hearn et al.

(10) Patent No.: US 7,361,178 B2
(45) Date of Patent: Apr. 22, 2008

(54) CRANIAL FLAP CLAMP AND INSTRUMENT FOR USE THEREWITH

(75) Inventors: James P. Hearn, Claymont, DE (US); John H. Manthorp, Downington, PA (US); Sean H. Kerr, Collegeville, PA (US)

(73) Assignee: Synthes (U.S.A.), West Chester, PA (US)

( * ) Notice: Subject to any disclaimer, the term of this patent is extended or adjusted under 35 U.S.C. 154(b) by 0 days.

(21) Appl. No.: 09/910,720

(22) Filed: Jul. 24, 2001

(65) Prior Publication Data

US 2002/0016593 A1    Feb. 7, 2002

Related U.S. Application Data

(60) Provisional application No. 60/221,148, filed on Jul. 27, 2000.

(51) Int. Cl.
*A61B 17/56* (2006.01)
*A61F 2/30* (2006.01)

(52) U.S. Cl. ...................................................... 606/72

(58) Field of Classification Search .................. 606/70, 606/71, 72, 73, 79, 60, 69, 151, 213, 215, 606/216, 232, 104; 403/279, 282; 24/704.1, 24/704.2, 713.6, 703.4, 703.6; 411/501, 411/512, 526, 544, 999
See application file for complete search history.

(56) References Cited

U.S. PATENT DOCUMENTS

| | | | |
|---|---|---|---|
| 276,135 A | 4/1883 | Cooley | |
| 460,222 A | 9/1891 | Silsby | |
| 601,399 A | 3/1898 | Manix | |
| 741,747 A | 10/1903 | Walz | |
| 891,509 A | 6/1908 | Tanner | |
| 1,918,700 A | 7/1933 | Harris | |
| 2,118,561 A | 5/1938 | Kleeberg | 85/37 |
| 2,291,413 A | 7/1942 | Siebrandt | 128/83 |
| 2,315,326 A | 3/1943 | Gmeiner | 128/340 |
| 2,316,297 A | 4/1943 | Southerland et al. | 128/326 |
| 2,340,995 A | 2/1944 | Smith | 128/321 |
| 2,485,531 A | 10/1949 | Dzus et al. | 128/92 |
| 2,576,649 A | 11/1951 | Slind et al. | |
| 3,038,626 A * | 6/1962 | Simmons | 29/243.522 |

(Continued)

FOREIGN PATENT DOCUMENTS

DE    1 089 116    9/1960

(Continued)

*Primary Examiner*—Anuradha Ramana
(74) *Attorney, Agent, or Firm*—Woodcock Washburn LLP

(57) ABSTRACT

The disclosed cranial flap clamp includes first and second clamping members and an extension member. A portion of the first member is positionable against inferior surfaces of a bone flap and skull and a portion of the second member is positionable against superior surfaces of the flap and skull. The extension member extends from the first member and fits between the flap and skull. The second member has a through opening for receiving the extension member. Movement of either of the clamping members urges the inner surface of the first member against the inferior surfaces of the flap and skull and urges the inner surface of the second member against the superior surfaces of the flap and skull. A stop provided by mechanical deformation of the extension member at any location along its length secures the clamp.

61 Claims, 5 Drawing Sheets

U.S. PATENT DOCUMENTS

| | | | | |
|---|---|---|---|---|
| 3,175,556 | A | 3/1965 | Wood et al. | 128/305 |
| 3,507,284 | A | 4/1970 | Simmons et al. | 128/318 |
| 3,971,384 | A | 7/1976 | Hasson | 128/335 |
| 4,050,464 | A | 9/1977 | Hall | |
| 4,088,134 | A | 5/1978 | Mazzariello | 128/321 |
| 4,452,246 | A | 6/1984 | Bader et al. | 128/340 |
| 4,644,953 | A | 2/1987 | Lahodny et al. | 128/305 |
| 4,669,473 | A | 6/1987 | Richards et al. | 128/334 |
| 4,736,494 | A * | 4/1988 | Marchesi | 24/303 |
| 4,763,669 | A | 8/1988 | Jaeger | 128/751 |
| 4,889,110 | A | 12/1989 | Galline et al. | 606/69 |
| 4,950,284 | A | 8/1990 | Green et al. | 606/216 |
| 5,030,050 | A * | 7/1991 | Auriol et al. | 411/38 |
| 5,059,193 | A | 10/1991 | Kuslich | 606/61 |
| 5,098,433 | A | 3/1992 | Freedland | 606/63 |
| 5,250,049 | A | 10/1993 | Michael | 606/72 |
| 5,258,015 | A | 11/1993 | Li et al. | 606/232 |
| 5,282,807 | A | 2/1994 | Knoepfler | 606/143 |
| 5,342,393 | A | 8/1994 | Stack | 606/213 |
| 5,346,500 | A | 9/1994 | Suchart | 606/138 |
| 5,350,399 | A | 9/1994 | Erlebacher et al. | 606/213 |
| 5,388,619 | A | 2/1995 | Ghawi | 140/123.6 |
| 5,392,822 | A | 2/1995 | Kraus | 140/123.6 |
| 5,468,242 | A | 11/1995 | Reisberg | |
| 5,478,353 | A | 12/1995 | Yoon | 606/213 |
| 5,538,427 | A | 7/1996 | Hoffman et al. | |
| 5,549,620 | A | 8/1996 | Bremer | 606/151 |
| 5,554,164 | A | 9/1996 | Wilson et al. | 606/167 |
| 5,562,694 | A | 10/1996 | Sauer et al. | 606/176 |
| 5,584,856 | A | 12/1996 | Jameel et al. | 606/220 |
| 5,591,176 | A | 1/1997 | Henderson et al. | 606/137 |
| 5,620,444 | A * | 4/1997 | Assaker | 606/61 |
| 5,643,289 | A | 7/1997 | Sauer et al. | 606/139 |
| 5,662,667 | A | 9/1997 | Knodel | 606/151 |
| 5,697,933 | A | 12/1997 | Gundlapalli et al. | 606/96 |
| 5,707,373 | A | 1/1998 | Sevrain et al. | 606/72 |
| 5,722,976 | A | 3/1998 | Brown | 606/69 |
| 5,725,553 | A | 3/1998 | Moenning | 606/213 |
| 5,757,801 | A | 5/1998 | Arimilli | 370/444 |
| 5,800,436 | A | 9/1998 | Lerch | 606/72 |
| 5,814,048 | A | 9/1998 | Morgan | |
| 5,814,055 | A | 9/1998 | Knodel et al. | 606/151 |
| 5,849,020 | A | 12/1998 | Long et al. | 606/167 |
| 5,860,993 | A | 1/1999 | Thompson et al. | 606/148 |
| 5,893,850 | A | 4/1999 | Cachia | 606/72 |
| 5,935,133 | A | 8/1999 | Wagner et al. | 606/103 |
| 5,944,723 | A | 8/1999 | Colleran et al. | 606/88 |
| 6,015,413 | A | 1/2000 | Faccioli et al. | 606/104 |
| 6,021,553 | A * | 2/2000 | Bieber et al. | 29/243.521 |
| 6,022,351 | A | 2/2000 | Bremer et al. | 606/72 |
| 6,033,429 | A | 3/2000 | Magovern | 606/216 |
| 6,068,631 | A | 5/2000 | Lerch | 606/72 |
| 6,123,711 | A | 9/2000 | Winters | 606/73 |
| 6,126,663 | A | 10/2000 | Hair | 606/72 |
| 6,168,596 | B1 | 1/2001 | Wellisz et al. | 606/69 |
| 6,197,037 | B1 | 3/2001 | Hair | 606/151 |
| 6,228,087 | B1 | 5/2001 | Fenaroli et al. | |
| 6,241,732 | B1 | 6/2001 | Overaker et al. | |
| 6,258,091 | B1 | 7/2001 | Sevrain et al. | 606/72 |
| 6,270,500 | B1 | 8/2001 | Lerch | 606/72 |
| 6,328,743 | B2 | 12/2001 | Lerch | |
| 6,361,538 | B1 | 3/2002 | Fenaroli et al. | |
| 6,371,958 | B1 | 4/2002 | Overaker | |
| 6,379,363 | B1 | 4/2002 | Herrington et al. | 606/79 |
| 6,485,493 | B1 | 11/2002 | Bremer | |
| 6,751,841 | B2 * | 6/2004 | Schnabel et al. | 29/524.1 |
| 2001/0011173 | A1 | 8/2001 | Lerch | 606/72 |
| 2001/0049529 | A1 | 12/2001 | Cachia et al. | 606/72 |
| 2002/0004661 | A1 | 1/2002 | Sevrain et al. | 606/73 |
| 2002/0016593 | A1 | 2/2002 | Hearn et al. | 606/72 |
| 2002/0029042 | A1 | 3/2002 | Fenaroli et al. | 606/73 |
| 2002/0040224 | A1 | 4/2002 | Lerch | 606/72 |
| 2002/0062128 | A1 | 5/2002 | Amis | 606/72 |
| 2002/0095156 | A1 | 7/2002 | Kuras et al. | 606/72 |
| 2002/0120274 | A1 | 8/2002 | Overaker et al. | 606/72 |
| 2002/0120281 | A1 | 8/2002 | Overaker | 606/151 |

FOREIGN PATENT DOCUMENTS

| | | |
|---|---|---|
| DE | 19634697 | 4/1998 |
| DE | 19634699 | 4/1998 |
| DE | 29812988 | 9/1998 |
| DE | 29812989 | 9/1998 |
| DE | 19832798 | 11/1999 |
| DE | 19952359 | 3/2001 |
| DE | 20101793 | 5/2001 |
| DE | 20109893 | 8/2001 |
| DE | 20109894 | 9/2001 |
| EP | 867149 | 9/1998 |
| JP | 9206311 A | 8/1997 |
| JP | 2000135230 A | 5/2000 |
| JP | 2002045367 | 2/2002 |
| JP | 2002065686 | 3/2002 |
| SU | 1419690 A | 8/1988 |
| SU | 1600713 A 1 | 10/1990 |
| WO | WO 98/46153 | 10/1998 |

* cited by examiner

CRANIAL FLAP CLAMP AND INSTRUMENT FOR USE THEREWITH

CROSS-REFERENCE TO RELATED APPLICATIONS

The benefit of Provisional Application Ser. No. 60/221,148 filed on Jul. 27, 2000 is claimed under 35 U.S.C. § 119(e).

FIELD OF THE INVENTION

The present invention is directed to a cranial flap clamp for attaching a bone flap to a skull and an instrument for use therewith.

BACKGROUND OF THE INVENTION

Craniotomies are surgical procedures performed in the treatment of various brain problems, such as tumors, aneurysms, blood clots, head injuries, abscesses, and the like. During a craniotomy procedure, access to the brain is achieved by the creation of a hole in the bone that defines the skull. The hole or "window" in the skull is usually created by identifying the area of the brain to which access is needed, drilling several holes into the skull near the periphery of this area, inserting a cutting tool into one of the holes, and making cuts from one hole to another. Removing the cut-out area of the skull, generally referred to as a bone flap, allows the desired access to the brain.

If all of the drilled holes are joined by cuts, such that the cuts form a complete outline of the "window", then the bone flap can simply be removed. Alternatively, if the cuts form only a partial outline of the window, the bone flap can be bent out of the way, in a hinge-like manner. Although the size and shape of the bone flap will vary with the desired cranial access area and size, a typical bone flap would be generally rectangular in shape and approximately four by six centimeters.

After the desired medical or surgical procedure on the brain has been performed, the bone flap must be replaced and held in a stable position to allow the skull to heal. There are many methods available for affixing the bone flap to the skull. One general method, for example, requires drilling pairs of holes in the edges of the skull and bone flap, threading wire through the holes, and twisting or tying the ends of the wire together to secure the edges of the bone flap to the skull. Disadvantages of this method include the tedious nature and length of time required for the procedure and the possibility of injury from drilling the holes too deep or from the sharp ends of the wires.

Another method of fixation generally involves the use of bone plates which are secured across the gaps between the bone flap and skull by screws. The disadvantages associated with the use of plates and screws relate to the undesirable cosmetic appearance resulting from the protrusion of the plate and screw above the bone surface. As there is minimal intervening soft tissue between the skull and the skin, unappealing external appearance is particularly a problem. The lack of soft tissue also has the unwanted consequence of permitting the patient to feel the plate and screw simply by pressing on the scalp. Thus, there is a need for improved devices for fixing a bone flap to a skull.

SUMMARY OF THE INVENTION

The present invention relates to a cranial flap clamp for fixing a bone flap to a skull. The clamp includes a first clamping member, an extension member, and a second clamping member. At least a portion of the inner surface of the first clamping member is positionable against inferior surfaces of the bone flap and skull and at least a portion of the inner surface of the second clamping member is positionable against superior surfaces of the bone flap and skull. The extension member extends from the first clamping member and is configured and dimensioned to fit between the bone flap and the skull. The second clamping member has an opening through its inner and outer surfaces for slidably receiving the extension member.

Movement of either or both of the first and second clamping members from a first position with the second clamping member distal to the first clamping member to a second position with the second clamping member proximal to the first clamping member urges the inner surface of the first clamping member against the inferior surfaces of the bone flap and skull and urges the inner surface of the second clamping member against the superior surfaces of the bone flap and skull. The cranial flap clamp also includes a stop provided by mechanical deformation of the extension member at a surgeon selected location along its length and adjacent the outer surface of the second clamping member when the first and second clamping members are in the second position to secure the inner surface of the first clamping member against the inferior surfaces of the bone flap and skull and the inner surface of the second clamping member against the superior surfaces of the bone flap and skull.

In order to reduce the risk of injury to the brain, the inner surfaces of the first and second clamping members can be substantially smooth. The inner surfaces of the first and second clamping members can be concave with the first and second clamping members in the first position and flatten out in the second position. The second clamping member may be provided with a disk shape having cutouts extending radially from the opening to provide resiliency.

In an exemplary embodiment, the extension member is a tube and the stop comprises a crimp in the tube. The extension member includes a head located at a distal end and the first clamping member includes a bore for slidably receiving the extension member. The head engages edges of the bore to prevent the first clamping member from sliding off the extension member. The tube can also have an enlarged portion near the inner surface of the first clamping member for preventing movement of the first clamping member along the tube away from the head. Finally, the tube can be provided with a flared proximal portion for preventing the second clamping member from sliding off the tube.

If the stop is formed by crimping, the opening can have a substantially circular shape which is smaller than the crimp. The opening can include a countersink for receiving the stop so that the stop fits substantially within the countersink.

In another exemplary embodiment, the extension member is a ribbon, which can be integral to the first clamping member, and the opening of the second clamping member has a rectangular shape. In this embodiment, the stop comprises a twisted portion of the ribbon. The second clamping member can be provided with a recessed area surrounding the opening so that the stop fits substantially within the recessed area. The recessed area has a width that increases from the center of the opening, a depth that increases from the center of the opening, and edges which form a cutting surface so that the stop may be formed by twisting and shearing of the ribbon.

The present invention also relates to a securing instrument for use with a cranial flap clamp. The securing instrument has first and second pivotally connected handles, a gripping arm operatively connected with the first handle, and a tensioning arm operatively connected with the second handle. The gripping and tensioning arms are movable in response to movement of the first and second handles and a slot extends through the distal portions of the gripping and tensioning arms for receiving the extension member of the cranial flap clamp. The securing instrument also includes a clamping element operatively associated with the slot. The clamping element has an inactive configuration, allowing sliding of the extension member through the slot, and an active configuration, clamping a portion of the extension member against a wall of the slot to inhibit sliding of the extension member through the slot. A crimping assembly is operatively associated with the arms for crimping the extension member.

In use, pivoting of the first and second handles causes the gripping and tensioning arms to separate with the tensioning arm engaging the outer surface of the second clamping member and the clamping element in the active position, thereby moving the first and second clamping members from the first position to the second position.

The clamping element can be a clamp rotatably coupled to the gripping arm so that rotation of the clamp within the slot upon separation of the gripping and tensioning arms moves the clamping element from the inactive configuration to the active configuration. Furthermore, a resilient member, such as a spring, can bias the clamping element in the active configuration when the gripping and tensioning arms are separated. The tensioning arm can include a foot with a ramped surface maintaining the clamping element in the inactive configuration when the gripping and tensioning arms are in contact.

In an exemplary embodiment, the crimping assembly comprises a slider having a crimping edge for crimping the extension member and sides configured and dimensioned for sliding in a grooved end of the tensioning arm, and a link operatively associated with the tensioning arm for sliding movement with respect thereto. The link has a distal end coupled to the slider and a proximal end with teeth. A lever is rotatably coupled to the tensioning arm and has a distal end with teeth engaging the teeth of the distal end of the link. The crimping assembly can also include a cutting stop that cooperates with the crimping edge of the slider to crimp and cut the extension member.

In order to isolate the distal end of the securing instrument so that only the distal end is in contact with the cranium, both the gripping and tensioning arms can have a curved or angled intermediate portion so that the distal portion of the gripping arm extends from the intermediate portion substantially parallel to the proximal portion.

A resilient element can be placed between the first and second handles, thereby biasing the first and second handles away from each other. In order to maintain the first and second handles at a given position, the securing instrument can include a locking bar having a first end pivotably coupled to the first handle and a curved body portion with a plurality of teeth and a locking clip pivotably coupled to the second handle and having a through channel. The locking clip is movable between a free position in which the locking bar is moveable in and out of the channel and a ratchet position in which the teeth of the locking bar engage an edge of the channel to prohibit the locking bar from moving out of the channel.

DESCRIPTION OF THE PREFERRED EMBODIMENTS

Figure 1:
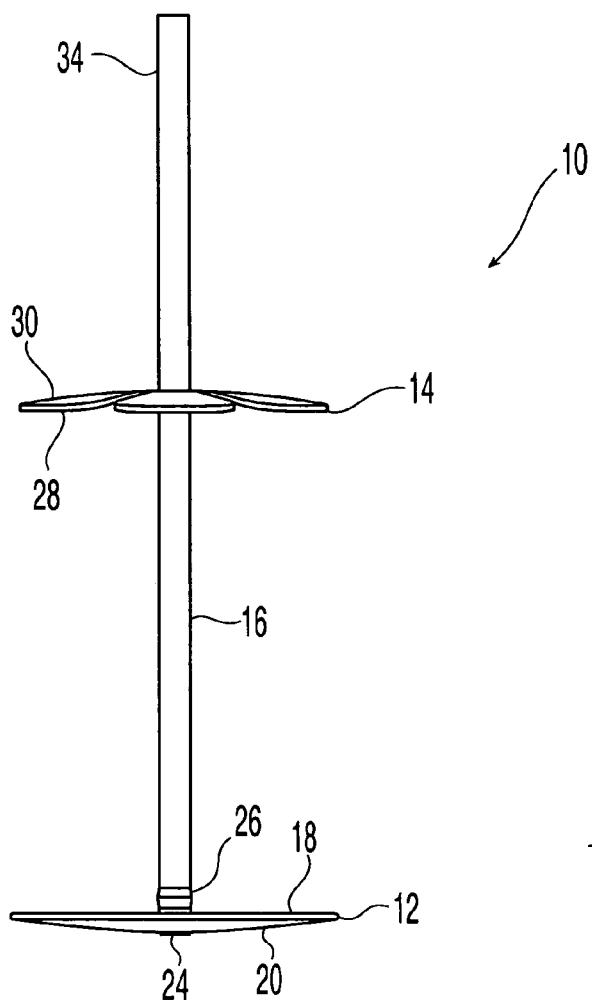
FIG. 1 is a perspective view of one embodiment of a cranial flap clamp according to the present invention.
Figure 2:
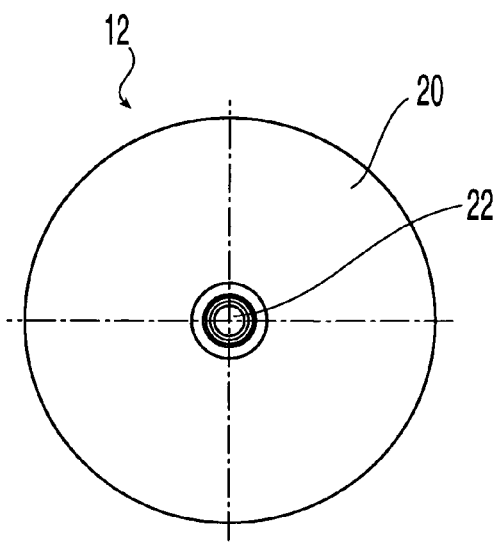
FIG. 2 is a top view of the outer surface of a first clamping member.

As shown in FIGS. 1-4, one embodiment of a cranial flap clamp 10 according to the present invention includes a first clamping member 12, a second clamping member 14, and an extension member 16. Cranial flap clamp 10 can be made of any suitable biocompatible material, such as stainless steel, titanium, a titanium based alloy, or a resorbable material. If cranial flap clamp 10 is made of a metallic material, preferably first and second clamping members 12, 14 and extension member 16 are made of the same material to minimize the potential for galvanic corrosion. First clamping member 12 has a disk shape with a concave inner surface 18 and a convex outer surface 20. Extension member 16 extends from inner surface 18 of first clamping member 12. Although extension member 16 is shown as a tube, extension member 16 can be any similar structure so long as the structure and material allow crimping, as explained below.

Extension member 16 can be integral to first clamping member 12. Alternatively, extension member 16 can be fastened to first clamping member 12 using any number of known ways. For example, first clamping member 12 can be provided with a bore 22 through which extension member 16 is inserted. A head 24 engages edges of bore 22 to prevent first clamping member 12 from sliding off extension member 16. Extension member 16 can be provided with an enlarged portion 26 near inner surface 18 of first clamping member 12 to prevent movement of first clamping member 12 along extension member 16 in a direction away from head 24. Enlarged portion 26 can be created, for example, by crimping. Alternatively, a ferrule or other similar component can be placed on extension member 16.

Second clamping member 14 also has a disk shape with a concave inner surface 28 and a convex outer surface 30. Second clamping member 14 is provided with an opening 32 through inner and outer surfaces 28, 30 for slidably receiving extension member 16. Because opening 32 slidably receives extension member 16, opening 32 and extension member 16 preferably have complimentary shapes. For example, if extension member 16 is a tube, then opening 32 preferably has a substantially circular shape. In order to prevent second clamping member 14 from sliding off extension member 16, extension member 16 can be provided with a flared proximal portion 34.

Figure 4:
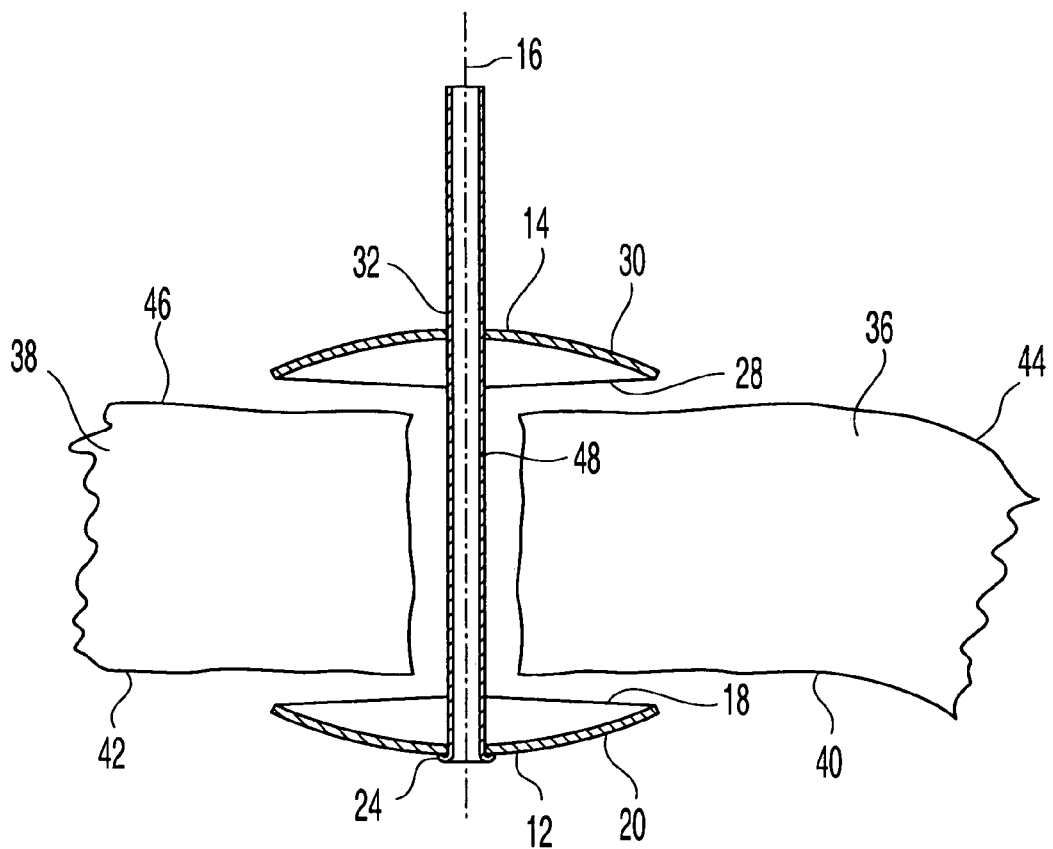
FIG. 4 is a cross sectional view of the cranial flap clamp of FIG. 1 implanted between a skull and a bone flap prior to crimping and cutting of the extension member.

In use, cranial flap clamp 10 fixes a bone flap 36 to a skull 38. FIG. 4 shows cranial flap clamp 10 in a first position. At least a portion of inner surface 18 of first clamping member 12 abuts an inferior surface 40 of bone flap 36 and an inferior surface 42 of skull 38. At least a portion of inner surface 28 of second clamping member 14 abuts a superior surface 44 of bone flap 36 and an superior surface 46 of skull 38. A portion of extension member 16 fits in a saw gap 48 between bone flap 36 and skull 38.

Figure 5:
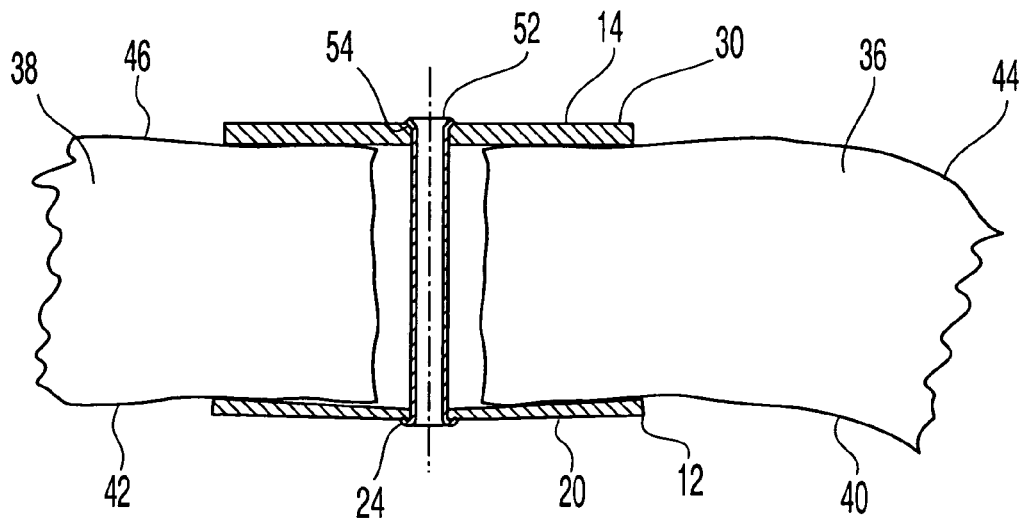
FIG. 5 is a cross sectional view of the cranial flap clamp of FIG. 4 after crimping and cutting of the extension member.
Figure 6:
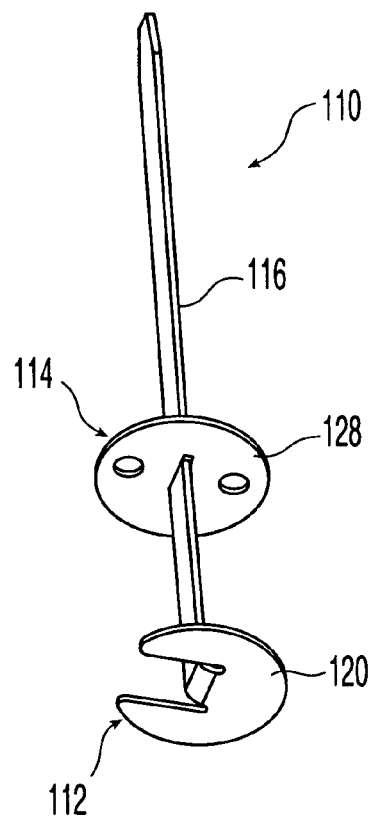
FIG. 6 is a perspective view of another embodiment of a cranial flap clamp according to the present invention.
Figure 7:
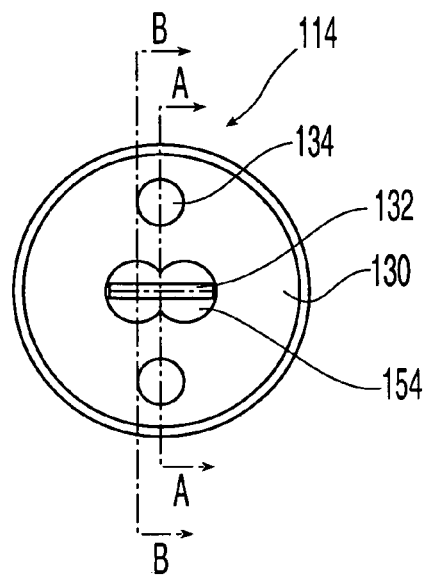
FIG. 7 is a top view of the outer surface of a second clamping member.

FIG. 5 shows cranial flap clamp 10 in a second position with first and second clamping member 12, 14 located more proximally to each other than the first position of FIG. 4. This movement (which can result from the movement of either or both of first and second clamping members 12, 14) urges inner surface 18 of first clamping member 12 against inferior surfaces 40, 42 of bone flap 36 and skull 38 and inner surface 28 of second clamping member 14 against superior surfaces 44, 46 of bone flap 36 and skull 38. There are a number of ways to move cranial flap clamp 10 from first position to second position. For example, extension member 16 can be pulled up while second clamping member 14 is pushed down. An instrument for performing these functions is described below.

Figure 3:
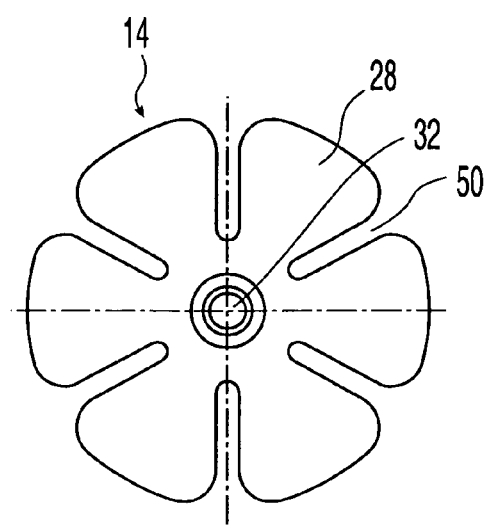
FIG. 3 is a top view of the inner surface of a second clamping member.

In order to minimize the risk of injury to the brain during implantation of cranial flap clamp 10, inner surfaces 18, 28 of first and second clamping members 12, 14 do not have teeth or similar surface features. In other words, inner surfaces 18, 28 are substantially smooth. If the inner surfaces of either or both of first and second clamping members 12, 14 are concave, then movement from the first position to the second position will tend to flatten out the inner surfaces so that more surface area contacts the inferior and/or superior surfaces of bone flap 36 and skull 38. In order to enhance this effect, either or both of first and second clamping member can be provided with radial cutouts. For example, FIG. 3 shows that second clamping member 14 has a plurality of radial cutouts 50 extending radially from opening 32.

Mechanical deformation of extension member 16 near outer surface 30 of second clamping member 14 with first and second clamping members 12, 14 in the second position forms a stop 52 to secure inner surface 18 of first clamping member 12 against inferior surfaces 40, 42 of bone flap 36 and skull 38 and inner surface 28 of second clamping member 14 against superior surfaces 44, 46 of bone flap 36 and skull 38. For cranial flap clamp 10, the mechanical deformation is crimping of extension member 16 near outer surface 30 of second clamping member 14. After the crimping, extension member 16 can be cut to remove any excess that extends substantially above second clamping member 14. Opening 32 of second clamping member 14 can include a countersink 54 (FIG. 3) for receiving stop 52. In an exemplary embodiment, stop 52 fits substantially within countersink 54 (FIG. 5).

FIGS. 6-11 show another embodiment of a cranial flap clamp 110 according to the present invention. Cranial flap clamp 110 includes a first clamping member 112, a second clamping member 114, and an extension member 116. Like cranial flap clamp 10, cranial flap clamp 110 can be made of any suitable biocompatible material, such as stainless steel, titanium, a titanium based alloy, or a resorbable material. If cranial flap clamp 110 is made of a metallic material, preferably first and second clamping members 112, 114 and extension member 116 are made of the same material to minimize the potential for galvanic corrosion. First clamping member 112 has a disk shape with an inner surface 118 and an outer surface 120. Extension member 116 extends from inner surface 118 of first clamping member 112. Although extension member 116 is shown as a ribbon, extension member 116 can be any similar structure so long as the structure and material allow shearing upon twisting against a suitable surface, as explained below.

As shown, extension member 116 is integral with first clamping member 112. Alternatively, extension member 116 can be fastened to first clamping member 112 using any number of known ways. Second clamping member 114 has a disk shape with an inner surface 128 and an outer surface 130 and an opening 132 through inner and outer surfaces 128, 130 for slidably receiving extension member 116. Because opening 132 slidably receives extension member 116, opening 132 and extension member 116 preferably have complimentary shapes. For example, if extension member 116 is a ribbon, then opening 132 preferably has a substantially rectangular shape. In order to prevent second clamping member 114 from sliding off extension member 116, extension member 116 can be provided with a flared proximal portion.

Figure 10:
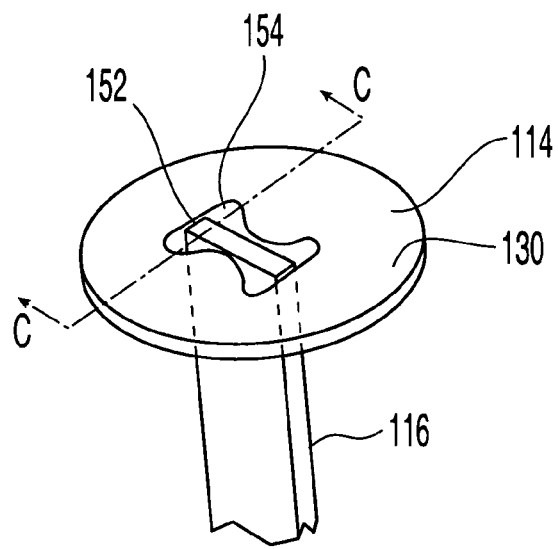
FIG. 10 is a perspective view of the second clamping member of FIG. 7 after twisting and shearing of the extension member.
Figure 11:
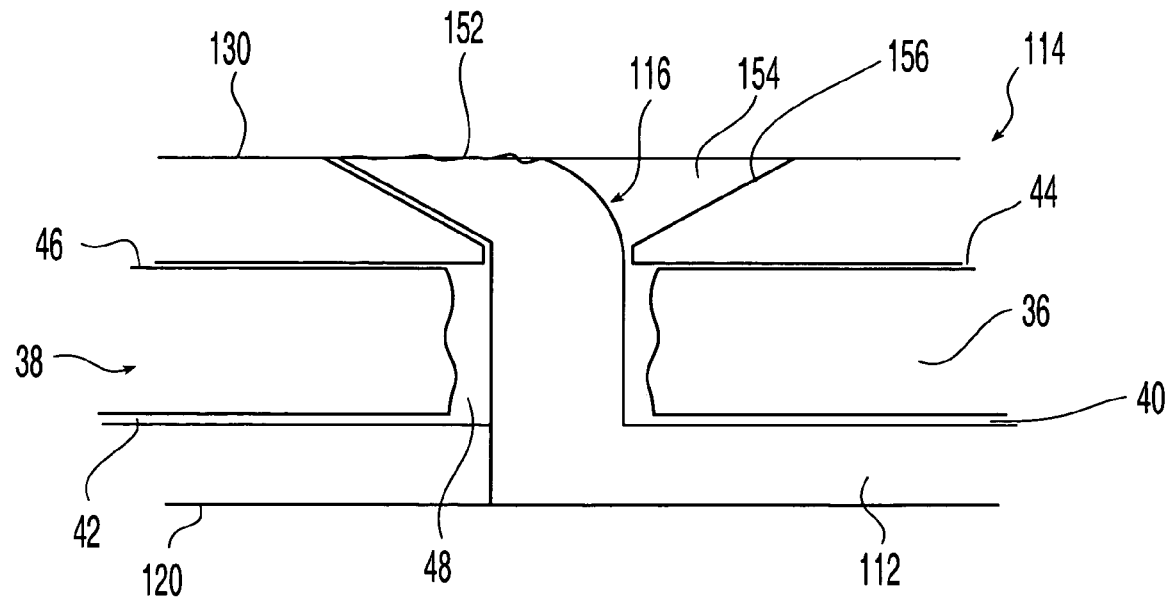
FIG. 11 is a cross sectional view taken along line C-C of FIG. 10 showing the cranial flap clamp implanted.

In use, cranial flap clamp 110 works in a manner analogous to cranial flap clamp 10 and fixes bone flap 36 to skull 38 by drawing first and second clamping members 112, 114 closer together, thereby urging inner surface 118 of first clamping member 112 against inferior surfaces 40, 42 of bone flap 36 and skull 38 and inner surface 128 of second clamping member 114 against superior surfaces 44, 46 of bone flap 36 and skull 38. As best seen in FIGS. 10 and 11, mechanical deformation of extension member 116 near outer surface 130 of second clamping member 114 with first and second clamping member 112, 114 in the second position forms a stop 152 to secure inner surface 118 of first clamping member 112 against inferior surfaces 40, 42 of bone flap 36 and skull 38 and inner surface 128 of second clamping member 114 against superior surfaces 44, 46 of bone flap 36 and skull 38. Second clamping member 114 can be provided with a fastener hole or holes 134 for receiving a fastener, such as a screw, for an additional mechanism to secure second clamping member 114 to bone flap 36 and skull 38.

Figure 8:
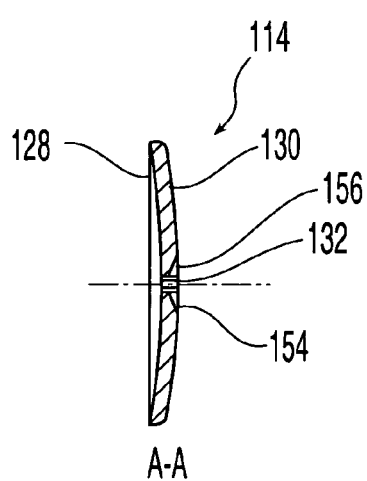
FIG. 8 is a cross sectional view taken along line A-A of FIG. 7.
Figure 9:
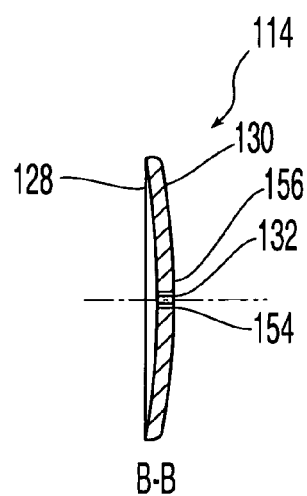
FIG. 9 is a cross sectional view taken along line B-B of FIG. 7.

For cranial flap clamp 110, the mechanical deformation is shearing of extension member 116. In particular, extension member 116 is twisted near outer surface 130 of second clamping member 114 with the first and second clamping members 112, 114 in the second position. A recessed area 154 surrounding opening 132 has edges that form a cutting surface 156 for shearing extension member 116 upon twisting to form stop 152. One geometry to form cutting surface 156 is achieved if recessed area 154 has a width that increases from the center of opening 132 and a depth that also increases from the center of opening 132, as best seen in FIGS. 8 and 9. In an exemplary embodiment, stop 152 fits substantially within recessed area 154 to minimize the profile of cranial flap clamp 110 after implantation.

Figure 12:
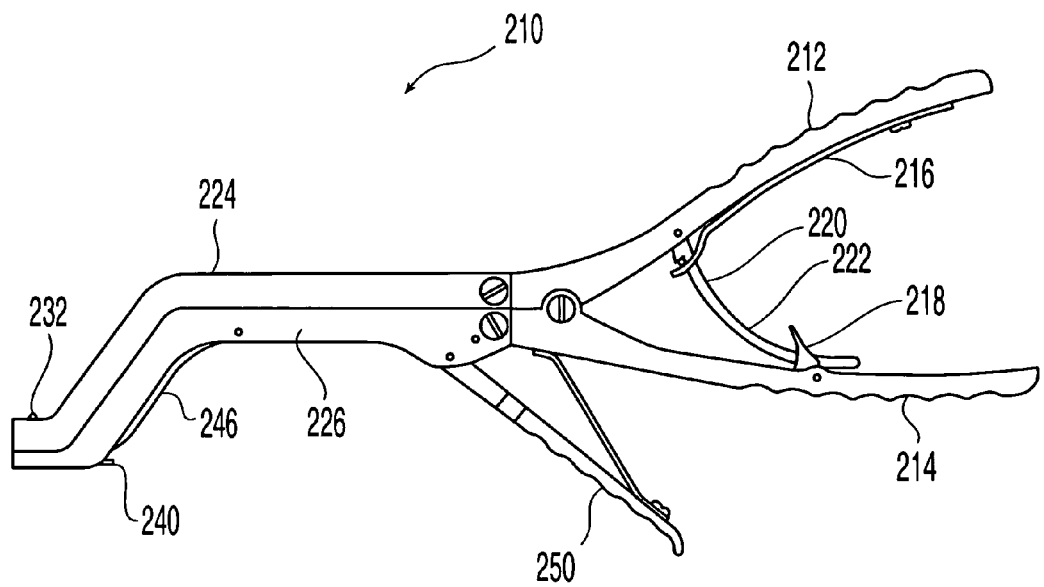
FIG. 12 is side view of a securing instrument for use with the cranial flap clamp according to the present invention.
Figures 13, 14:
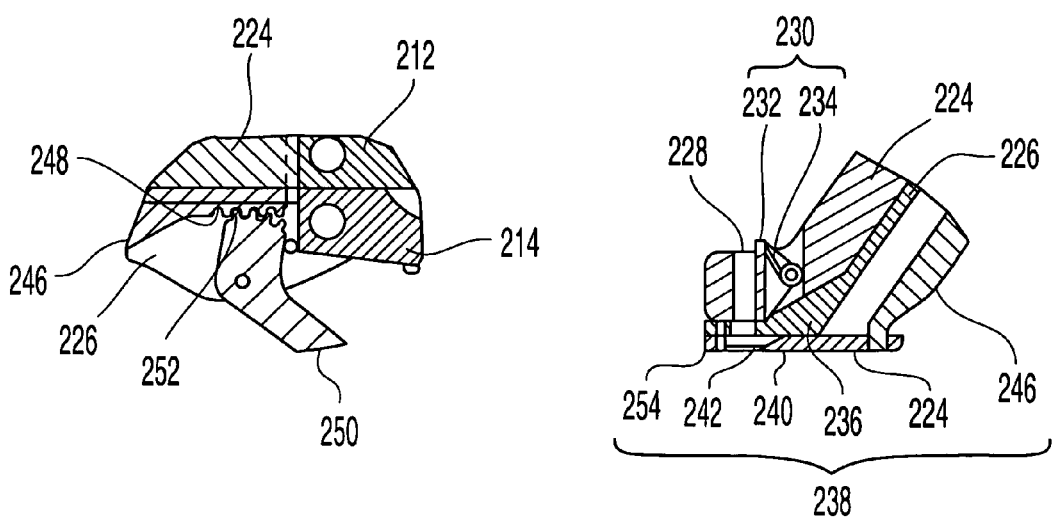
FIG. 13 is a cross sectional view of the distal portion of the securing instrument of FIG. 12.
FIG. 14 is a cross sectional view of the proximal portion of the gripping arm of the securing instrument of FIG. 12.

FIGS. 12-14 show a securing instrument 210 for implantation of the cranial flap clamp according to the present invention. Although instrument 210 can be used with either cranial flap clamp 10, 110, instrument 210 is particularly useful with cranial flap clamp 10. Securing instrument 210 includes first and second handles 212, 214. First and second handles 212, 214 are pivotably connected such that upon squeezing, the distal ends of first and second handles 212, 214 spread apart from each other. A resilient element 216, such as a leaf spring, is located between first and second handles 212, 214 and biases their proximal ends away from each other so that upon releasing of the squeezing pressure, the distal ends of first and second handles 212, 214 pivot back toward each other until contact.

A locking mechanism can be provided to resist the biasing force of resilient element 216. For example, a locking clip 218 is located on second handle 214 and is movable between a free position in which a locking bar 220 is free to move through a channel in locking clip 218 and a ratchet position in which locking bar 220 can only move through locking clip 218 in one direction. This ratchet mechanism allows first and second handles 212, 214 to maintain their relative positions after squeezing and release of the squeezing pressure. In order to create the ratchet effect, a portion of locking bar 220 can be provided with teeth 222 that engage an edge of the channel when locking clip 218 is in the ratchet position.

A gripping arm 224 is operatively connected with first handle 212 and a tensioning arm 226 is operatively connected with second handle 214. Gripping and tensioning arms 224, 226 are movable in response to movement of the first and second handles. Thus, as first and second handles 212, 214 are squeezed, gripping and tensioning arms 224, 226 separate or spread apart from each other.

A slot 228 extends through the distal portions of gripping and tensioning arms 224, 226 for receiving the extension member of the cranial flap clamp. Gripping and tensioning arms 224, 226 can be made as straight extensions from the distal ends of their respective handle. In an exemplary embodiment, however, each of gripping and tensioning arms 224, 226 has a curved body portion with the distal end of securing instrument 210 isolated from the rest of the instrument, so that in use, only the distal end of securing instrument 210 is in contact with the cranium.

A clamping element 230 is operatively associated with slot 228. Clamping element 230 has an inactive configuration in which extension member can freely slide through slot 228 and an active configuration in which a portion of extension member is clamped against a wall of slot 228 to inhibit sliding of the extension member through slot 228. Clamping element 230 includes a clamp 232 rotatably coupled to gripping arm 224. Rotation of clamp 232 within slot 228 upon separation of gripping and tensioning arms 224, 226 moves clamping element 230 from the inactive configuration to the active configuration. A resilient member 234 biases clamping element 230 in the active configuration when gripping and tensioning arms 224, 226 are separated. Tensioning arm 226 includes a foot 236 with a ramped surface maintaining clamping element 230 in the inactive configuration when gripping and tensioning arms 224, 226 are in contact.

In order to crimp the extension member after proper positioning, a crimping assembly 238 is operatively associated with tensioning arm 226. Alternatively, crimping assembly 238 can be associated with gripping arm 224. In an exemplary embodiment, a slider 240 has a crimping edge 242 for crimping the extension member and sides 244 configured and dimensioned for sliding in a grooved end of tensioning arm 226. A link 246 is operatively associated with tensioning arm 226 so that link 246 can slide with respect to tensioning arm 226. Link 246 has a distal end coupled to slider 240 and a proximal end with teeth 248. A lever 250 has a distal end rotatably coupled to tensioning arm 226. The distal end of lever 250 is provided with teeth 252 that engage teeth 248 of the distal end of link 246. As lever 250 is pivoted, the engagement of teeth 248, 252 causes the pivoting to be translated to sliding motion of link 246 and slider 240. A leaf spring or other similar mechanism can be used to cause lever 250 to pivot back. Crimping assembly 238 can also include a cutting stop 254 cooperating with crimping edge 242 of slider 240 to crimp and cut the extension member.

In use, extension member is inserted into slot 228 and securing instrument 210 is moved down toward the cranium with the cranial flap clamp in the position shown in FIG. 4. First and second handles 212, 214 are pivoted to cause gripping and tensioning arms 224, 226 to move away from each other. This movement causes tensioning arm 226 to push against the outer surface of the second clamping member and clamping element 230 to be in the active position, thereby holding the extension member and drawing the first clamping member toward the second clamping member. With the first and second clamping members in the second position, crimping assembly 238 can be used to crimp and cut the extension member.

The invention described and claimed herein is not to be limited in scope by the specific embodiments herein disclosed, since these embodiments are intended solely as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A cranial flap clamp for fixing a bone flap to a skull comprising:
   a first clamping member having inner and outer surfaces, at least a portion of the inner surface positionable against inferior surfaces of the bone flap and skull;
   a substantially smooth extension member extending from the first clamping member and configured and dimensioned to fit between the bone flap and the skull; and
   a second clamping member having inner and outer surfaces and an opening through the inner and outer surfaces for slidably receiving the extension member, with at least a portion of the inner surface positionable against superior surfaces of the bone flap and skull, the opening having a recessed area forming a cutting surface; wherein:
   the first and second clamping members have a first position of the second clamping member distal to the first clamping member and a second position of the second clamping member proximal to the first clamping member that urges the inner surface of the first clamping member against the inferior surfaces of the bone flap and skull and urges the inner surface of the second clamping member against the superior surfaces of the bone flap and skull;
   the inner surfaces of the first and second clamping members are concave in the first position and flatten out in the second position;

the second clamping member has a disk shape with a plurality of cutouts extending radially inward from an outer circumference of the second clamping member; and the extension member comprises an integrally formed stop on the extension member adjacent the outer surface of the second clamping member after the first and second clamping members are in the second position to secure the inner surface of the first clamping member against the inferior surfaces of the bone flap and skull and the inner surface of the second clamping member against the superior surfaces of the bone flap and skull, the stop sized and configured to fit substantially within the recessed area.

2. The cranial flap clamp of claim 1, wherein the extension member is integral with the first clamping member.

3. The cranial flap clamp of claim 1, wherein the first clamping member comprises a bore for receiving the extension member.

4. The cranial flap clamp of claim 3, further comprising a head disposed on the extension member for slidably engaging the bore to prevent the first clamping member from sliding off the extension member.

5. The cranial flap clamp of claim 1, wherein, the extension member includes a flared proximal portion for preventing the second clamping member from sliding off.

6. The cranial flap clamp of claim 1 wherein the second clamping member has at least one fastener hole for receiving a fastener.

7. The cranial flap clamp of claim 1 wherein the portions of the first and second clamping members that abut the inferior surfaces of the bone flap and skull are substantially smooth.

8. A cranial flap clamp for fixing a bone flap to a skull comprising:
a first clamping member having inner and outer surfaces, at least a portion of the inner surface positionable against inferior surfaces of the bone flap and skull;
a smooth extension member extending from the first clamping member and configured and dimensioned to fit between the bone flap and the skull; and
a second clamping member having inner and outer surfaces and an opening through the inner and outer surfaces for slidably receiving the extension member, with at least a portion of the inner surface positionable against superior surfaces of the bone flap and skull; wherein:
movement of at least one of the first and second clamping members from a first position of the second clamping member distal to the first clamping member to a second position of the second clamping member proximal to the first clamping member urges the inner surface of the first clamping member against the inferior surfaces of the bone flap and skull and urges the inner surface of the second clamping member against the superior surfaces of the bone flap and skull;
the second clamping member is fixed with respect to the extension member by a crimping force applied to the extension member adjacent the second clamping member; and
the second clamping member has a plurality of cutouts extending radially inwards from an outer circumference of the second clamping member so that the inner surface of the second clamping member is concave when the first and second clamping members are in the first position and the inner surface of the second clamping member flattens out when the first and second clamping members are in the second position.

9. The cranial flap clamp of claim 8, wherein the extension member is a tube and the stop comprises a crimp in the tube.

10. The cranial flap clamp of claim 9 wherein the extension member includes a head located at a distal end and the first clamping member includes a bore for slidably receiving the extension member, the bore comprising edges that engage the head of the extension member to prevent the first clamping member from sliding off the extension member.

11. The cranial flap clamp of claim 10 wherein the tube has an enlarged portion near the inner surface of the first clamping member for preventing movement of the first clamping member along the tube away from the head.

12. The cranial flap clamp of claim 9 wherein, when the first and second clamping members are in the first position, the tube includes a flared proximal portion for preventing the second clamping member from sliding off the tube.

13. The cranial flap clamp of claim 9 wherein the opening has a substantially circular shape which is smaller than the crimp.

14. The cranial flap clamp of claim 13 wherein the opening includes a countersink for receiving the stop and the stop fits substantially within the countersink.

15. The cranial flap clamp of claim 8, wherein the extension member is integral with the first clamping member.

16. The cranial flap clamp of claim 8, wherein the second clamping member has at least one fastener hole for receiving a fastener.

17. The cranial flap clamp of claim 8, wherein the portions of the first and second clamping members that abut the inferior surfaces of the bone flap and skull are substantially smooth.

18. A cranial flap clamp for fixing a bone flap to a skull comprising:
a first clamping member having inner and outer surfaces, at least a portion of the inner surface positionable against inferior surfaces of the bone flap and skull;
an extension member extending from the first clamping member and configured and dimensioned to fit between the bone flap and the skull, the extension member being smooth and comprising a stop located at a surgeon selected location along the length of the extension member; and
a second clamping member having inner and outer surfaces and an opening through the inner and outer surfaces for slidably receiving the extension member, with at least a portion of the inner surface positionable against superior surfaces of the bone flap and skull, wherein:
movement of at least one of the first and second clamping members from a first position of the second clamping member distal to the first clamping member to a second position of the second clamping member proximal to the first clamping member urges the inner surface of the first clamping member against the inferior surfaces of the bone flap and skull and urges the inner surface of the second clamping member against the superior surfaces of the bone flap and skull; and
at least one of the clamping members has a plurality of radial cutouts extending radially inwards from an outer circumference of the clamping member so that movement of the clamping member from the first position to the second position causes the inner surface of the clamping member to flatten out allowing the clamping member to at least partially conform to the outer surface of the bone flap and skull.

19. The cranial flap clamp of claim 18 wherein the extension member is integral with the first clamping member.

20. The cranial flap clamp of claim 18 wherein the second clamping member has at least one fastener hole for receiving a fastener.

21. The cranial flap clamp of claim 18, wherein the extension member is a ribbon and the opening of the second clamping member has a rectangular shape.

22. The cranial flap clamp of claim 21 wherein the stop comprises a twisted portion of a ribbon.

23. The cranial flap clamp of claim 22 wherein the second clamping member is provided with a recessed area surrounding the opening, wherein the stop fits substantially within the recessed area.

24. The cranial flap clamp of claim 23 wherein the recessed area forms a cutting surface so that the stop may be formed by twisting and shearing of the ribbon.

25. The cranial flap clamp of claim 18, wherein the first clamping member comprises a bore for receiving the extension member.

26. The cranial flap clamp of claim 25, further comprising a head disposed on the extension member for slidably engaging the bore to prevent the first clamping member from sliding off the extension member.

27. The cranial flap clamp of claim 26, wherein the extension member includes a flared proximal portion for preventing the second clamping member from sliding off.

28. The cranial flap clamp of claim 18, wherein the extension member is a tube and the stop comprises a crimp in the tube.

29. The cranial flap clamp of claim 28, wherein the opening has a substantially circular shape that is smaller than the crimp.

30. The cranial flap clamp of claim 29, wherein the opening includes a countersink for receiving the stop and the stop fits substantially within the countersink.

31. The cranial flap clamp of claim 30, wherein the second clamping member comprises a recessed area proximate the opening for receiving the stop.

32. The cranial flap clamp of claim 18, wherein the portions of the first and second clamping members that abut the inferior surfaces of the bone flap and skull are substantially smooth.

33. A cranial flap clamp for fixing a bone flap to a skull comprising:
a first clamping member positionable against inferior surfaces of the bone flap and skull;
a smooth extension member extending from the first clamping member and configured and dimensioned to extend between the bone flap and the skull;
a second clamping member positionable against superior surfaces of the bone flap and skull and comprising an opening in which a portion of the extension member is disposed and a recessed area forming a cutting surface proximate the opening; and
an integrally formed stop on the extension member abutting the second clamping member for limiting movement of the second clamping member when the first clamping member abuts the inferior surfaces and the second clamping member abuts the superior surfaces;
wherein:
the portions of the first and second clamping members that abut the inferior surfaces of the bone flap and skull are substantially smooth;
the first and second clamping members each comprise a disk shape; and
the second clamping member further comprises a plurality of cutouts extending radially inwards from an outer circumference of the second clamping member.

34. The cranial flap clamp of claim 33, wherein the extension member comprises a tube and the stop comprises a crimp in the tube.

35. The cranial flap clamp of claim 34, wherein the opening has a substantially circular shape that is smaller than the crimp.

36. The cranial flap clamp of claim 33, further comprising a head disposed on the extension member proximate the first clamping member.

37. The cranial flap clamp of claim 33, wherein the first clamping member comprises a bore for receiving the extension member.

38. The cranial flap clamp of claim 33, wherein the opening comprises a countersink and the stop is disposed substantially within the countersink.

39. The cranial flap clamp of claim 33, wherein the first and second clamping members each comprise an arcuate outer edge.

40. The cranial flap clamp of claim 33, wherein the extension member comprises a ribbon.

41. The cranial flap clamp of claim 40, wherein the stop comprises a twisted portion of the ribbon.

42. The cranial flap clamp of claim 33, wherein the stop comprises a twisted portion of the extension member.

43. The cranial flap clamp of claim 33, wherein the stop is received in the recessed area.

44. The cranial flap clamp of claim 33, wherein the extension member is integral with the first clamping member.

45. The cranial flap clamp of claim 33, wherein the second clamping member comprises at least one fastener hole for receiving a fastener.

46. The cranial flap clamp of claim 33, wherein the stop is provided by mechanical deformation of the extension member at a surgeon selected location along its length.

47. A cranial flap clamp for fixing a bone flap to a skull comprising:
a first clamping member;
a smooth extension member extending from the first clamping member;
a second clamping member having a first surface and a second surface opposite the first surface, the first surface facing the first clamping member and positionable against superior surfaces of the bone flap and skull, the second clamping member having a through hole extending from the first surface to the second surface, the extension member extending through the hole to at least the second surface, the second clamping member having a plurality of radial cutouts extending radially inwards from an outer circumference of the second clamping member; and
an integrally formed stop on the extension member for limiting movement of the second clamping member on the extension member.

48. The cranial flap clamp of claim 47, wherein the extension member is integral with the first clamping member.

49. The cranial flap clamp of claim 47, wherein opposing surfaces of the first and second clamping members are substantially smooth.

50. The cranial flap clamp of claim 47, wherein the first and second clamping members each have a concave inner surface.

51. The cranial flap clamp of claim 47, wherein the first and second clamping members each have an inner surface capable of flattening out upon fixation to a bone flap and skull.

52. The cranial flap clamp of claim 47, wherein at least one of the first and the second clamping members is disk shaped.

53. The cranial flap clamp of claim 47, wherein the extension member is a ribbon and the through hole of the second clamping member has a rectangular shape.

54. The cranial flap clamp of claim 53, wherein the stop comprises a twisted portion of the ribbon.

55. The cranial flap clamp of claim 47, wherein the extension member is a tube and the stop comprises a crimp in the tube.

56. The cranial flap clamp of claim 47, wherein the second clamping member comprises a recessed area proximate the through hole for receiving the stop.

57. The cranial flap clamp of claim 56, wherein the recessed area forms a cutting surface so that the stop may be formed by twisting and shearing of the extension member.

58. The cranial flap clamp of claim 47, wherein the first clamping member comprises a bore for receiving the extension member.

59. The cranial flap clamp of claim 58, wherein the extension member comprises a head disposed thereon for slidably engaging the bore to prevent the first clamping member from sliding off the extension member.

60. The cranial flap clamp of claim 47, wherein the extension member includes a flared proximal portion for preventing the second clamping member from sliding off.

61. The cranial flap clamp of claim 47, wherein the through hole includes a countersink for receiving the stop and the stop fits substantially within the countersink.

* * * * *